(12) United States Patent
Makita et al.

(10) Patent No.: US 6,528,078 B1
(45) Date of Patent: Mar. 4, 2003

(54) PEST REPELLENT COMPOSITION

(75) Inventors: Mitsuyasu Makita, Nishinomiya (JP); Tadahiro Matsunaga, Kobe (JP)

(73) Assignee: Sumitomo Chemical Company, Limited, Osaka (JP)

( * ) Notice: Subject to any disclaimer, the term of this patent is extended or adjusted under 35 U.S.C. 154(b) by 52 days.

(21) Appl. No.: 09/263,795

(22) Filed: Mar. 5, 1999

(30) Foreign Application Priority Data

Mar. 31, 1998 (JP) ............................................. 10-086973

(51) Int. Cl.[7] ........................ A01N 25/00; A01N 31/00; A61K 31/045
(52) U.S. Cl. .................. 424/405; 424/45; 424/489; 424/DIG. 8; 424/DIG. 10; 514/919; 514/729
(58) Field of Search ................................ 424/405, 489, 424/45, DIG. 10, DIG. 8; 514/729, 919

(56) References Cited

U.S. PATENT DOCUMENTS 5,698,209 A * 12/1997 Shono et al. ............... 424/405
6,346,261 B1 * 2/2002 Sembo ....................... 424/405

OTHER PUBLICATIONS

AN–97–545447 [50] WPIDS; abstract of JP 09263501.
AN 85–307846 [49] WPIDS; abstract of JP 60215092.
AN 88–063905 [09] WPIDS; abstract of JP WO 8801164.
AN 84–316290 [51] WPIDS, abstract of JP 59199602.

* cited by examiner

*Primary Examiner*—Sabiha Qazi
(74) *Attorney, Agent, or Firm*—Birch, Stewart, Kolasch & Birch, LLP

(57) ABSTRACT

Pest repellents are provide that contain a pest repellent composition comprising carane-3,4-diol as an active ingredient, a non-porous round polyethylene powder, and a solvent. Preferably, the provided pest repellent compositions comprise (i) about 3–50% by weight of carane-3,4-diol, (ii) about 3-30% by weight of a paraffin, (iii) about 20–90% by weight of an alcohol and (iv) a non-porous round polyethylene powder, wherein the amount of the non-porous round polyethylene powder present in the pest repellent composition is about 0.05 to 1.0 times the weight of carane-3,4-diol present in the composition. Aerosol pest repellents are also provided.

16 Claims, No Drawings

PEST REPELLENT COMPOSITION

FIELD OF THE INVENTION

The present invention relates to a pest repellent composition, and more particularly to such compositions containing carane-3,4-diol as an active ingredient therein.

BACKGROUND OF THE INVENTION

Convenient pest repellents have been developed as pest thwarting compositions, which compositions are either utilized by directly spraying or spreading onto the human body. U.S. Pat. No. 5,130,136, which is incorporated herein by reference in its entirety, discloses carane-3,4-diol as an effective active ingredient for pest repellents, but pest repellents containing carane-3,4-diol have several deficiencies despite the ability of carane-3,4-diol to efficiently repel pests. One of said deficiencies lies with the adhesive character of carane-3,4-diol. Specifically, the adhesive character of carane-3,4-diol often causes a viscid sensation similar to the feeling of having a film of sweat covering the body (hereinafter referred to as an "adhesive feeling") when a pest repellent which contains carane-3,4-diol is applied to the body. Because such an adhesive feeling is undesirable, pest repellents comprising inorganic or organic powders have been proposed to lessen the adhesive feelings associated with carane-3,4-diol pest repellent compositions. However, when such pest repellent compositions comprising powders are applied to the body, they often produce the visually unappealing effect of having a white powder sprinkled onto the applied surface (hereinafter referred to as a "whitening" effect).

The convenience with which such a pest repellent can be used is additionally diminished when the pest repellent comprises a powder. For example, when utilized in a spraying device, powders within a spray or aerosol composition can often cause obstructions inside pumps, valves, tubes, and/or at the nozzle of an atomizer, so that the spraying device cannot dispense the pest repellent composition efficiently. Further, because powders within the aerosol composition of the pest repellent composition can also tend to settle at the bottom of the spraying device, difficulties are also encountered in evenly redistributing powders after the they have settled at the bottom of the device.

The above deficiencies that are associated with prior known pest repellents are problematic. The above deficiencies are also especially troublesome in that such pest repellents can be inconvenient to utilize, whereas spraying devices are typically known and relied upon for their ease of use. Accordingly, the present invention is concerned with providing an effective pest repellent composition that can overcome the prior encountered problems in the art of adhesive feeling, whitening, and inconvenience.

SUMMARY OF THE INVENTION

The present invention provides for a pest repellent composition that may be formulated as an aerosol composition or as a liquid composition. More particularly, the present invention provides for aerosol and liquid pest repellent compositions that comprise a non-porous round polyethylene powder, a solvent, and carane-3,4-diol as a pest repelling active ingredient. The provided aerosol compositions additionally contain a propellant. The inventive composition overcome the prior encountered problems of adhesive feeling, whitening, and at the same time are convenient to utilize. For example, the present inventive compositions allow for spraying to be performed smoothly without encountering any problems of adhesive feeling, whitening or clogging of the spray or aerosol apparatus with which they are applied to a body surface.

DETAILED DESCRIPTION OF THE INVENTION

The pest repellent composition of the present invention may be formulated as a liquid composition or as an aerosol composition that contains said liquid composition in combination with a propellant, to thereby repel objective pests. Examples of the objective pests that can be repelled with the inventive compositions are the blood-sucking insects/acarina such as mosquitoes (Culicidae), black flies (Simuliidae), stable flies (Stomoxyidae), sand flies, biting midges (Ceratopogonidae), and the like.

The pest repellent compositions of the present invention contain carane-3,4-diol, which is a highly effective but oily and highly adhesive active ingredient. In the case that the pest repellent composition of the present invention is in the form of a liquid, the liquid preferably comprises carane-3,4-diol in an amount of about 3% to 50% by weight, more preferably about 4% to 45% by weight, and most preferably about 5% to 40% by weight, based on the total weight of the liquid composition.

The solvent employed in the liquid compositions of the instant invention preferably contains paraffin (or isoparaffin) and alcohol, but is not limited thereto, since other conventional solvents are also well known to those skilled in the art.

Preferably, the liquid compositions of the present invention comprise as a solvent, paraffin (or isoparaffin) in an amount of about 3% to 30% by weight, more preferably about 5% to 25% by weight, and an alcohol at an amount of about 20% to 90% by weight, preferably about 50% to 85% by weight, based on the total weight of the liquid composition.

The term "paraffin" as used herein means a saturated aliphatic hydrocarbon having the formula $C_nH_{2n+2}$, and includes straight chain paraffins (i.e. normal-paraffin) and branched chain paraffins (i.e. isoparaffin). As such, either normal-paraffins or isoparaffins may be employed as a solvent ingredient in the inventive compositions. Isoparaffin is preferably used as an ingredient in the solvent of the present inventive compositions. The carbon number of the employed paraffin or isoparaffin is preferably 4 to 20, and more preferably 4 to 15. Furthermore, the selected solvent may contain a mixture of miscellaneous paraffins, if so defined. For example, commercially available isoparaffins that may be employed as a solvent or a solvent ingredient in the present invention include IP Solvent, IP-1016, IP-1620, IP-2028 (product names from Idemitsu Petrochemical Company Ltd.), Isopar E, Isopar G, Isopar H (product names from Exxon Chemical Company), and so on.

The solvent used to produce one of the inventive compositions should preferably also comprise an alcohol such as a $C_{1-8}$ lower alcohol, but the use of an alcohol is not mandatory in the present invention. Preferably, the chosen alcohol should possess the ability to fulfill cosmetic purposes. Accordingly, examples of alcohols that are useful as solvents in the present invention are ethyl alcohol, isopropyl alcohol, other $C_{1-8}$ lower alcohols and alcohols that have been denatured with perfumes such as ethanols denatured with Bitrex (Denatonium benzoate, Mac Pharen Smith Ltd.). Further, a mixture of such alcohols can also be used in the present invention, if so desired.

The non-porous round polyethylene powders, which may be employed in the inventive compositions, preferably contain copolymers comprising mainly ethylene units, such as an ethylenepropylene copolymer. However, other copolymers containing ethylene units may also be utilized in the invention, provided that their powders are round and non-porous. The particles of any such powders used in the inventive compositions should preferably have the dimensions of a generally spherical shape, and more preferably have an average diameter of about 5 µm to 30 µm, and more preferably of about 7 µm to 20 µm. The present invention preferably comprises the non-porous round polyethylene powder particles in an amount where the weight ratio between carane-3,4-diol and the non-porous round polyethylene powder particles is from about 1:0.05 to 1:1, preferably from about 1:0.1 to 1:0.6, on a weight to weight basis.

In addition, the inventive liquid compositions, in order to more effectively distribute powder in the solvent, may optionally contain a dispersing agent. Various surfactants may be utilized as the dispersing agent, with examples of such surfactants including sorbitan fatty acid ester sufactants such as sorbitan monooleate and sorbitan monolaurate, silicone-type surfactants such as a copolymer of dimethylsiloxane and methyl(polyoxyethylene)siloxane as well as a copolymer of dimethylsiloxane and methyl(polyoxyethylene-polyoxypropylene)siloxane, mixtures thereof, and the like. It is more preferable to incorporate silicone-type surfactants in the inventive liquid compositions, since silicone-type surfactants have the ability to noticably lessen the adhesive feeling of the pest repellent composition. When present, the amount of the dispersing agent within one of the inventive liquid compositions is preferably about 5.0% by weight or less, and more preferably about 3.0% by weight or less, based on the total weight of the liquid composition.

In the case that the liquid pest repellent composition is formulated into an aerosol, the inventive aerosol should comprise a propellant in combination with a liquid composition of the present invention. Examples of suitable propellants that may be employed to prepare an aerosol include liquefied petroleum gas, propane, propylene, n-butane, isobutane, n-pentane, isopentane, dimethyl ether, carbon dioxide, compressed gases such as nitrogen gas, a mixture thereof, and the like. The propellant may be incorporated in the inventive compositions in an amount so that the ratio of weight of the liquid composition to the propellant is preferably from about 9:1 to 2:8, and more preferably from about 8:2 to 3:7, on a weight to weight basis.

Additionally, a preferable spraying system for an aerosol of the present invention is to utilize a device having a spray opening of a spraying button of about 0.4 mm to 1.1 mm, an inner diameter of a stem orifice of about 0.4 mm to 0.7 mm, a vapor tap orifice of about 0.5 mm to 0.7 mm, and an inner diameter of a dip tube of about 1 mm to 1.6 mm.

Preparation of one of the inventive liquid pest repellent compositions can be achieved by simply mixing each of the ingredients together, but a mixing method, wherein a shaking or stirring step is employed, may also be advantageously used to promote re-dispersibility of the prepared liquid or aerosol pest repellent. Moreover, while mixing of the liquid pest repellent composition may be performed by any suitable means (e.g. a high speed stirrer such as a homogenizer), it is preferable to utilize a device wherein ultrasonic waves are emitted (e.g. ultrasonic emitter) to obtain an even distribution of the powder within the liquid. Further, an aerosol of the present invention may be prepared by dispersing the non-porous round polyethylene powder in the liquid composition, before the propellant and the liquid composition are packed into an aerosol container, but it is also possible to load each ingredient of the liquid composition and the propellant into an aerosol container and subsequently disperse the powder by the use of a device such as an ultrasonic emitter. The time necessary to sufficiently distribute the non-porous round polyethylene powder in one of the inventive liquid or aerosol compositions differs upon the amount of pest repellent ingredient employed and the ratio between the amount of each ingredient in the inventive liquid or aerosol composition, but usually for about 2 to 10 minutes, and preferably about 3 to 7 minutes is necessary when the ultrasonic emitter is utilized at the frequencies of about 20 to 150 kHz, and the size of the composition is from about 50 mL to 150 mL.

A pest repellent composition of the present invention may also comprise as optional ingredients, fragrances, fungicides, coloring agents, humidity control agents, ulta-violet light absorbers, anti-oxidents and the like, if so desired, provided that the pest repellent composition still repels pests, does not provide whitening or adhesive feeling and remains convenient to utilize.

EXAMPLES

Hereinafter, the present invention is explained more specifically with regard to the following examples, but is not limited thereto.

Liquid Composition Test Methods (1) Re-dispersibility Test

The liquid compositions of the following Examples 1–7 or the liquid compositions of the following Comparative Examples 1–3 are each allowed to settle for 2 hours, after preparing said liquid compositions and placing in a screw-top vial. The screw-top vial containing the liquid composition is then rotated upside-down and returned to its upright position 10 times by hand. Thereafter, a "+" score is given when the powders disperse in the liquid by said rotations, and a "−" score is given when the powder still remains settled at the bottom area of the vial.

(2) Adhesive Feeling Test

Three-tenths milliliters (0.3 mL) of the liquid composition from Comparative Example 1 is spread to an area of about 6 cm×6 cm on the skin of the left arm. The liquid compositions from Examples 1–7 or the liquid compositions from Comparative Examples 2–3 are each spread in the same way on the right arm and allowed to dry for 5 minutes. The adhesive feeling for each Example and Comparative Example is then examined by determining the sensation that the finger s or the palm of the other hand acquires when palpating each sample. The adhesive feeling of the samples from Examples 1–7 and Comparative Examples 2–3, which are dispensed on the right arm, are compared to the sample from Comparative Example 1, and are given a score based on the adhesive feeling of Comparative Example 1. A "−" score is given to samples when the adhesive feeling of the sample was at the same level or higher than Comparative Example 1; a "+" score is given to samples with a lower adhesive feeling than that of Comparative example 1; and a "++" score is given to samples with an even lower adhesive feeling than inventive samples achieving a "+" score.

(3) Whitening Test

The test compositions are dispensed in the same way as was done for the adhesive feeling tests above and are allowed to dry for 30 minutes. The dried surfaces on which the compositions are spread are then observed for the appearance of whitening. A "+" score is given to samples wherein an indication of whitening is not visually noticed, and a "−" score is given to samples wherein whitening or any viewable remnants of the liquid composition is visually noticable on the spread surface.

Example 1

Five grams (5 g) of carane-3,4-diol, 5 g of a $C_{8-14}$ isoparaffin, 0. 5 g of a non-porous round polyethylene powders, and an ethanol denatured with Bitrex (Denatonium benzoate, MacPharen Smith Ltd.) are deposited into a screw-top vial (Maruem Company Type No.8) so that the mixture in total aggregates to 45 g. The mixture is subjected to magnetic stirring for 10 min., and thereafter to ultrasonic waves with a Branson 3200 ultrasonic emitter (Yamato sciences) for 5 minutes at the frequency of 47 kHz to sufficiently stir the mixture and obtain a liquid composition of the present invention.

The obtained liquid composition is tested according to a re-dispersibility test, adhesive feeling test, and whitening test by using the methods recited above. The results are given in Table 1–1, below.

Examples 2–7 and Comparative Examples 1–3

The liquid compositions of Examples 2–7 and Comparative Examples 1–3 are obtained in a like manner to Example 1 except the amount of carane-3,4-diol, variation and amount of paraffin or isoparaffin, type and amount of powder, type of alcohols, duration of stirring, and duration of ultrasonic emission are altered according to the conditions set forth in Table 1–1 or Table 1–2, below.

The obtained liquid compositions of the invention are tested according to a re-dispersibility test, adhesive feeling test, and whitening test by using the methods recited above. The results are provided in Tables 1–1 and 1–2, below.

TABLE 1-1

| Exp. No. | Example 1 | Example 2 | Example 3 | Example 4 | Example 5 |
|---|---|---|---|---|---|
| Carane-3,4-diol (g) | 5 | 5 | 5 | 15 | 5 |
| Isoparaffin Type | ① | ① | ① | ④ | ① |
| Isoparaffin Amount (g) | 5 | 5 | 5 | 5 | 5 |
| Powder Type | ② | ② | ② | ② | ② |
| Powder Amount (g) | 0.5 | 1 | 3 | 3 | 1 |
| Alcohol Type | ③ | ③ | ③ | ③ | ③ |
| Stirring Time (min) | 10 | 10 | 10 | 10 | 30 |
| Ultrasonic Emission (min) | 5 | 5 | 5 | 5 | 0 |
| Re-dispersibility | + | + | + | + | + |
| Adhesive Feeling | + | ++ | ++ | + to ++ | + to ++ |
| Whitening | + | + | + | + | + |

TABLE 1-2

| Exp. No. | Example 6 | Example 7 | Comparative Example 1 | Comparative Example 2 | Comparative Example 3 |
|---|---|---|---|---|---|
| Carane-3,4-diol (g) | 5 | 5 | 5 | 5 | 5 |
| Isoparaffin Type | ① | ④ | | ① | ① |
| Isoparaffin Amount (g) | 5 | 10 | 0 | 5 | 5 |
| Powder Type | ⑤ | ② | | | ⑦ |
| Powder Amount (g) | 1 | 1 | 0 | 0 | 1 |
| Alcohol Type | ⑥ | ③ | ③ | ③ | ③ |
| Stirring Time (min) | 10 | 10 | 30 | 30 | 10 |
| Ultrasonic Emission (min) | 5 | 5 | 0 | 0 | 5 |
| Re-dispersibility | + | + | transparent | transparent | + |
| Adhesive Feeling | ++ | ++ | adhesive | − | + to ++ |
| Whitening | + | + | + | + | − |

①Isoparaffin (Carbon number of 8–14)
②Non-porous, Spherical polyethylene powders, average diameter 7 μm
③Ethanol denatured with Bitrex (Denatonium benzoate, MacPharen Smith Ltd.)

TABLE 1-2-continued

| Exp. No. | Example 6 | Example 7 | Comparative Example 1 | Comparative Example 2 | Comparative Example 3 |
|---|---|---|---|---|---|

④Isoparaffin (Carbon number of 4–10)
⑤Non-porous spherical polyethylene powders, average diameter 20 μm
⑥Isopropyl Alcohol
⑦Hollow, Cross-linked, Non-porous, Round Polymethyl methacrylate Powders, average diameter 20–50 μm Aerosol Composition Test Methods (1) Re-Dispersibility Test The aerosol compositions of Examples 8–14 and Comparative Examples 4–5 are each allowed to settle for 2 hours, after preparing each aerosol composition in a pressured glass container. The pressured glass container comprising the aerosol composition is then slowly rotated 10 times by hand. A "+" score is given when the powder disperses in the liquid by the rotations, and a "−" score is given when the powder remains settled at the bottom area of the pressured glass container.

(2) Adhesive Feeling Test

The aerosol composition of Comparative Example 4 is spread onto the skin of the left arm by spraying at a distance of 8cm away for a duration of 3 seconds. The aerosol compositions from Examples 8–14 or Comparative Example 5 are spread onto the skin of the right arm in the same way and allowed to dry for 5 minutes. The adhesive feeling of each sample is then examined by determining the sensation that the fingers or the palm of the other hand acquire when palpating each sample. The samples dispensed on the right arm are compared with the sample from Comparative Example 4, and are given a score based on the adhesive feeling of Comparative Example 4. A "−" score is given to samples when the adhesive feeling of the sample was at the same level or higher than Comparative Example 4, a "+" score is given to samples with a lower adhesive feeling than Comparative Example 4, and a "++" score is given to samples with an even lower adhesive feeling than the samples achieving a "+" score in the test.

(3) Whitening Test

The test compositions are dispensed in the same way as was done for the adhesive feeling tests for the aerosol compositions as described above, and are allowed to dry for 30 minutes. The dried surfaces are then observed for the appearance of whitening. A "+" score is given to samples wherein an indication of whitening is not visually noticed, and a "−" score is given to samples wherein whitening or any viewable remnants of the dispensed particles are visually noticed on the sprayed surface.

Example 8

Twenty-two and one half grams (22.5 g) of the liquid composition of Example 1 is deposited into a glass pressure-vessel (100 mL Nihon Kohbunshi Company) and an aerosol valve is then affixed to the said vessel. Twenty-seven and one-half grams (27.5 g) of a liquefied petroleum gas that is 2 kg/cm$^2$ .G at 20° C., is packed as the propellant so that the aerosol composition is obtained. The obtained aerosol composition is utilized for a re-dispersibility test, adhesive feeling test, and whitening according to the test methods recited above. The results are given in Table 2-1, below.

Examples 9–14 and Comparative Examples 4–6

The aerosol compositions of Examples 9–14 and Comparative Examples 4–6 are obtained in a like manner to Example 8 except the liquid compositions are altered as shown in Table 2-1 and 2-2. The obtained aerosol compositions are subjected to a re-dispersibility test, adhesive feeling test, and whitening test by using the methods recited in Example 8. The results are given in Tables 2-1 and 2-2.

TABLE 2-1

|  | Example 8 | Example 9 | Example 10 | Example 11 | Example 12 |
|---|---|---|---|---|---|
| Liquid Composition | Example 1 | Example 2 | Example 3 | Example 4 | Example 5 |
| Re-dispersibility | + | + | + | + | + |
| Adhesive Comfort | + | ++ | ++ | + to ++ | + to ++ |
| Whitening | + | + | + | + | + |

TABLE 2-2

|  | Example 13 | Example 14 | Comparative Example 4 | Comparative Example 5 | Comparative Example 6 |
|---|---|---|---|---|---|
| Liquid Composition | Example 6 | Example 7 | Comparative Example 1 | Comparative Example 2 | Comparative Example 3 |
| Re-dispersibility | + | + | Transparent | Transparent | + |
| Adhesive Comfort | ++ | ++ | adhesive | − | + |
| Whitening | + | + | + | + | − |

Test Examples 1–12

The liquid compositions or the aerosol compositions of Examples 1–4, 6–11, or 13–14 are allowed to settle for 2 hours after the preparation of each composition in a glass pressure-vessel. The glass pressure-vessel for spraying is slowly rotated 3 times by hand, and re-dispersibility is observed. A "+" score is given to the powders that disperse in the composition by the said rotations, and a "−" score is given when the powder settles at the bottom area of the glass pressure-vessel or when the powder does not disperse equivalently.

TABLE 3-1

| Test Example No. | 1 | 2 | 3 | 4 | 5 | 6 |
|---|---|---|---|---|---|---|
| Utilized Liquid Composition or Aerosol Composition | Example 1 | Example 2 | Example 3 | Example 4 | Example 6 | Example 7 |
| Re-dispersibility | + | + | + | + | + | + |

TABLE 3-2

| Test Example No. | 7 | 8 | 9 | 10 | 11 | 12 |
|---|---|---|---|---|---|---|
| Utilized Oil Ingredient or Aerosol Composition | Example 8 | Example 9 | Example 10 | Example 11 | Example 13 | Example 14 |
| Re-dispersibility | + | + | + | + | + | + |

Example 15

Two and one-half grams (2.5 g) of carane-3,4-diol, 2.5 g of a $C_{8-14}$ isoparaffin and ethanol denatured with Bitrex (Denatonium benzoate, MacPharen Smith Ltd.) are mixed to provide 22 g of a liquid mixture. Twenty-two grams (22 g) of the liquid mixture and 0.5 g of non-porous spherical polyethylene powder are deposited into a glass pressure-vessel (100 mL Nihon Kohbunshi Company) and an aerosol valve is affixed to the vessel. Subsequently, 27.5 g of a liquefied petroleum gas that is 2 kg/cm² .G at 20° C., is packed into the vessel as the propellant. After gently shaking the contents inside the vessel, the contents of the vessel are subjected to ultrasonic waves from a Branson 3200 ultrasonic emitter (Yamato sciences) for 5 min at 47 kHz, to provide an aerosol composition. Each obtained aerosol composition is subjected to a re-dispersibility test using the method recited in Test Example 1, and an adhesive feeling test and whitening test by following the method recited in Example 8. The results are given in Table 4, below.

Examples 16–17

The aerosol compositions of Examples 16–17 are obtained in a like manner to Example 15 except that the amount of carane-3,4-diol, variation and amount of the powder, amount of isoparaffin, amount of mixing liquid (the preparation with alcohol), and the packing amount of the liquefied petroleum gas are altered to fit the conditions set forth in Table 4. The re-disperability tests, adhesive feelings, and whitening tests for the obtained aerosol compositions are performed by using the methods recited in Example 15

TABLE 4

| | Example 15 | Example 16 | Example 17 |
|---|---|---|---|
| Powder Variation | ② | ③ | ② |
| Powder Amount (g) | 0.5 | 0.2 | 1 |
| Carane-3,4-diol (g) | 2.5 | 1 | 5 |
| Isoparaffin Amount (g) | 2.5 | 1 | 5 |
| Alcohol Variation | ②c | ④ | ② |
| Liquid Mixture Amount (g) | 22 | 8.8 | 44 |
| Packing Liquid Petroleum Gas (g) | 27.5 | 8.8 | 5 |

TABLE 4-continued

| | Example 15 | Example 16 | Example 17 |
|---|---|---|---|
| Re-dispersibility | + | + | + |
| Adhesive Comfort | ++ | ++ | ++ |
| Whitening | + | + | + |

①: Isoparaffin (Carbon number of 8–14)
②: Non-porous, Spherical polyethylene powders, average diameter 7 μm
③: Ethanol denatured with Bitrex (Denatonium benzoate, MacPharen Smith Ltd.)
④: Isoparaffin (Carbon number of 4–10)

What is claimed is:

1. A pest repellent composition comprising an effective pest repelling amount of carane-3,4-diol as an ingredient, a non-porous round polyethylene powder, and a solvent.

2. The pest repellent composition according to claim 1, wherein the solvent contains a paraffin or an alcohol.

3. The pest repellent composition according to claim 2, wherein said paraffin is an isoparaffin.

4. The pest repellent composition according to claim 2, wherein said alcohol is a $C_{1-8}$ lower alcohol.

5. The pest repellent composition according to claim 1, wherein the ratio of the carane-3,4-diol to the non-porous round polyethylene powder is from about 1:0.05 to 1:1.0, on a weight to weight basis.

6. A liquid pest repellent composition, which comprises
   (i) 3–50% by weight of carane-3,4-diol,
   (ii) 3–30% by weight of a paraffin or a mixture of paraffins,
   (iii) 20–90% by weight of an alcohol or a mixture of alcohols, and
   (iv) a non-porous round polyethylene powder.

7. The liquid pest repellent composition according to claim 6, wherein the ratio of carane-3,4-diol to the non-porous round polyethylene powder is from about 1:0.05 to 1:1, on a weight to weight basis.

8. An aerosol pest repellent, which comprises a propellant and a pest repellent composition containing an effective pest repelling amount of carane-3,4-diol, a non-porous round polyethylene powder and a solvent.

9. The aerosol pest repellent according to claim 8, wherein the solvent contains a paraffin or an alcohol.

10. The aerosol pest repellent according to claim 9, wherein said paraffin is an isoparaffin.

11. The aerosol pest repellent according to claim 9, wherein said alcohol is a $C_{1-8}$ lower alcohol.

12. The aerosol pest repellent according to claim 8, wherein the ratio of the pest repellent composition to the propellant is from about 9:1 to 2:8, on a weight to weight basis.

13. An aerosol pest repellent comprising a propellant and pest repellent composition containing the following ingredients (i) to (iv):

(a) 3–50% by weight of carane-3,4-diol, (ii) 3–30% by weight of a paraffin, (iii) 20–90% by weight of an alcohol, and (iv) a non-porous round polyethylene powder.

14. The aerosol pest repellent according to claim 8, wherein ratio of the pest repellent composition to the propellant is from about 9:1 to 2:8, on a weight to weight basis.

15. The pest repellent composition according to claim 1, wherein said non-porous polyethylene powder comprises particles having the dimensions of a generally spherical shape.

16. The pest repellent composition according to claim 1, wherein said non-porous polyethylene powder comprise particles comprising an average diameter of from about 5 $\mu$m to 30 $\mu$m.

* * * * *